(12) United States Patent
Chen et al.

(10) Patent No.: US 8,153,680 B2
(45) Date of Patent: Apr. 10, 2012

(54) ALKYL INDOLE-3-CARBINOL-DERIVED ANTITUMOR AGENTS

(75) Inventors: Ching-Shih Chen, Upper Arlington, OH (US); Jing-Ru Weng, Taichung (TW)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 12/547,036

(22) Filed: Aug. 25, 2009

(65) Prior Publication Data

US 2011/0054002 A1     Mar. 3, 2011

(51) Int. Cl.
*A61K 31/404*     (2006.01)
*C07D 209/04*     (2006.01)

(52) U.S. Cl. ........................ 514/415; 548/509
(58) Field of Classification Search ................. 514/415; 548/509
See application file for complete search history.

(56) References Cited

U.S. PATENT DOCUMENTS

| | | | |
|---|---|---|---|
| 6,656,963 B2 | 12/2003 | Firestone et al. | |
| 6,800,655 B2 | 10/2004 | Jong et al. | |
| 7,078,427 B2 | 7/2006 | Jong et al. | |
| 7,807,705 B2 | 10/2010 | Chen et al. | |
| 2005/0043385 A1 | 2/2005 | Guy et al. | |
| 2006/0223890 A1 | 10/2006 | Ramakrishna et al. | |
| 2008/0300291 A1 | 12/2008 | Chen et al. | |

FOREIGN PATENT DOCUMENTS

| | | |
|---|---|---|
| GB | 1490671 | 11/1997 |
| WO | 98/50357 | 11/1998 |
| WO | 2004/048330 | 6/2004 |
| WO | 2004/055026 | 7/2004 |
| WO | 2008/144263 | 11/2008 |

OTHER PUBLICATIONS

Golub et al. Science (1999), vol. 286 521-537.*
Lala et al. Cancer and Metastasis Reviews (1998), 17(1), 91-106.*
Office action from U.S. Appl. No. 12/118,591 dated Nov. 18, 2009.
Response from U.S. Appl. No. 12/118,591 dated Jul. 7, 2009.
Office action from U.S. Appl. No. 12/118,591 dated Apr. 7, 2009.
International Search Report from PCT/US08/63323 dated Oct. 13, 2008.
Aggarwal et al., "Molecular Targets and anticancer potential of indole-e-carbinol and its derivatives"; Cell Cycle 4.9, pp. 1201-1215; Sep. 2005.
Allen et al., "Entry into 6-methoxy-D(+)-tryptophans. Stereospecific synthesis of 1-benzenesulfonyl-6-methoxy-D(=)-tryptophan ethyl ester", Synthetic Communications 1992, US, vol. 22, No. 14, pp. 2077-2102 (1992).
Bell et al., "Placebo-controlled trial of indole-3-carbinol in the treatment of CIN", Gynecol Oncol, 78: 123-129 (2000).
Brandi et al., "A new indole-e-carbinol tetrameric derivative inhibits cyclin-dependent kinase 6 expression, and induces G1 cell cycle arrest in both estrogen-dependent and estrogen-independent breat cancer cell lines", Cancer Research 63: pp. 4028-4036, Jul. 15, 2003.

Bradlow et al., "Effects of dietary indole-e-carbinol on estradiol metabolism and spontaneous mammary tumors in mice", Carcinogenesis, 12: 1571-1574 (1991).
Chinni et al., "Indole-3-carbinol (I3C) induced cell growth inhibition, G1 cell cycle arrest and apoptosis in prostate cancer cells", Oncogene, 20: pp. 2927-2936 (2001).
Chinni et al., "Akt inactivation is a key event in indole-3-carbinol-induced apoptosis in PC-3 cells", Clinical Cancer Research, vol. 8, pp. 1228-1236, Apr. 2002.
Chintharlapalli et al., "1,-1-Bis(3'-indolyl)-1-(p-substitutedphenyl)methanes induce peroxisome proliferator-activated receptor γ-mediated growth inhibition, transactivation, and differentiation markers in colon cancer cells", Cancer Research 64: 5994-6001, Sep. 1, 2004.
Chintharlapalli et al., "1,1-Bis(3'-indolyl)-1-(p-substitutedphenyl)methanes are peroxisome Proliferator-activated receptor Y agonists but decrease HCT-116 colon cancer cell survival through receptor-independent activation of early growth response-1 and nonsteroidal anti-inflammatory drug-activated gene-1", Molecular Pharmacology, vol. 68, No. 6, pp. 1782-1792 (2005).
Contractor et al., "A novel ring-substituted diindolylmethane, 1,1-Bis[3'-(5-methoxyindolyl)]-1-(p-t-butylphenyl) methane, inhibits extracellular signal-regulated kinase activation and induces apoptosis in acute myelogenous leukemia", Cancer Res. 65: 7: pp. 2890-2898, Apr. 1, 2005.

(Continued)

*Primary Examiner* — Rebecca Anderson
*Assistant Examiner* — Samantha Shterengarts
(74) *Attorney, Agent, or Firm* — Calfee, Halter & Griswold LLP

(57) ABSTRACT

Compounds and methods for treating cancer or inducing apoptosis in proliferating cells. The compounds are shown in formula I:

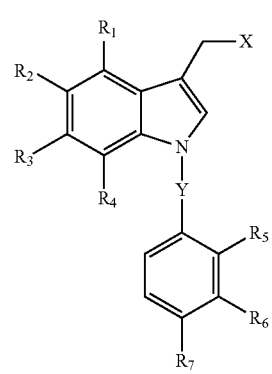

wherein X is selected from hydroxyl, thiol, and amino; Y is selected from carboxyl and sulfonyl; $R_1$, $R_2$, $R_3$, and $R_4$ are selected from hydrogen, lower alkyl, and combinations thereof; $R_5$, $R_6$, and $R_7$ are selected from hydrogen, halo, nitro, amino, methoxy, and combinations thereof; and pharmaceutically acceptable salts thereof.

13 Claims, 9 Drawing Sheets

OTHER PUBLICATIONS

Cover et al., "Indole-3-carbinol and tamoxifen cooperate to arrest the cell cycle of MCF-7 human breast cancer cells", Cancer Res. 59: 1244-1251 (1999).

Dekruif et al., Structure elucidation of acid reaction products of indole-3-carbinol: detection in vio and enzyme induction in vitro, Chem Biol Interact, 80: p. 303-315 (1991).

Dropinski et al., "Synthesis and biological activities of novel aryl indole-2-carboxylic acid analogs as PPARγ partial agonists", Bioorganic & Medicinal Chemistry Letters 15: pp. 5035-5038 (2005).

Gribble et al., "Syntheses and Diels-Alder cycloaddition reactions of 4H-furo[3,4-b]indoles. A regiospecific Diels-Alder synthesis of ellipticine", J. of Organic Chemistry, vol. 57, No. 22, U.S., pp. 5878-5891 (1992).

Grose et al., "Oligomerization of indole-3-carbinol in aqueous acid", Chem Res Toxicol, 5: pp. 188-193 (1992).

Grubbs et al., "Chemoprevention of chemically-induced mammary carcinogenesis by indole-3-carbinol", Anticancer Res 15: 709-716 (1995).

He et al., "Indole-3-carbinol as a chemopreventive agent in 2-amino-1-methyl-6-phenylimidazo[4,5-b]pyridine (PhIP) carcinogenesis: inhibition of PhIP-DNA adduct formation, acceleration of PhIP metabolism, and induction of cytochrome P450 in female F344 rats", Food Chem Toxicol 38: 15-23 (2000).

Henke et al., "Synthesis and biological activity of a novel series of indole-derived PPARγ agonists", Bioorganic & Medicinal Chemistry Letters, 9: pp. 3329-3334 (1999).

Howells et al., "Inhibition of phosphatidylinositol 3-kinase/protein kinase B signaling is not sufficient to account for indole-3-carbinol-induced apoptosis in some breast and prostate tumor cells", Clinic Cancer Res. 11: 23: pp. 8521-8527, Dec. 1, 2005.

Hsu et al., "Indole-3-carbinol inhibition of androgen receptor expression and downregulation of androgen responsiveness in human prostate cancer cells", Carcinogenesis, vol. 26, No. 11, pp. 1896-1904 (2005).

Jin et al., "Indole-3-carbinol prevents cervical cancer in human papilloma virus type 16 (HPV16) transgenic mice", Cancer Re. 59: 3991-3997 (1999).

Kassouf et al., "Inhibition of bladder tumor growth by 1,1-Bis(3'-indolyl)-1-(p-substitutedphenyl)methanes: a new class of peroxisome proliferator-activated receptor γ agonists", Cancer res. 66: 1: pp. 412-418, Jan. 1, 2006.

Kim et al., "Targets for indole-3-carbinol in cancer prevention", J of Nutritional Biochemistry, 16: pp. 65-73 (2005).

Kojima et al., "Chemoprevention of spontaneous endometrial cancer in female Donryu rats by dietary indole-3-carbinol in the treatment of CIN", Gynecol Oncol, 78: 123-129 (2000).

Kondo et al., "Halogen-Magnesium exchange reaction of iodoindole derivatives", Heterocycles, vol. 42, No. 1, pp. 105-108, 1996.

Kutschy et al., "New synthesis of indole phytoalexins and related compounds", Tetrahedron, Elsevier Science Publishers, Amsterdam, NL, vol. 54, No. 14, pp. 3549-3566 (Apr. 2, 1998).

Manson, "Inhibition of survival signalling by dietary polyphenols and indole-3-carbinol", European J of Cancer, 41: pp. 1842-1853 (2005).

Nachshon-Kedmi et al., "Indole-3-carbinol and 3,3'-diindolylmethane induce apoptosis in human prostate cancer cells", Food and Chemical Toxicology, 41: pp. 745-752 (2003).

Naik et al., "A randomized phase II trial of indole-3-carbinol in the treatment of vulvar intraepithelial neoplasia", Int J Gynecol Cancer 16: 786-790 (2006).

Oganesian et al., "Long term dietary indole-3-carbinol inhibits diethylnitrosamine-initiated hepatocarcinogenesis in the infant mouse model", Cancer Lett, 118: 87-94 (1997).

Qin et al., "A new class of peroxisome proliferator-activated receptor γ (PPARγ) agonists that inhibit growth of breast cancer cells: 1,1-Bis(3'-indolyl)-1-(p-substituted phenyl)methanes", Molecular Cancer Therapeutics, 3: 3: pp. 247-259, (2004).

Reed et al., "A phase I study of indole-3-carbinol in women: tolerability and effects", Cancer Epidemiol Biomarkers Prev. 14: 1953-1960 (2005).

Reed et al., "Single-dose and multiple-dose administration of indole-3-carbinol to women: pharmacokinetics based on 3,3'-diindolylmethane", Cancer Epidemiol Biomarkers Prev, 15: 2477-2481 (2006).

Rogan, Eg "The natural chemopreventive compound indole-3-carbinol: state of the science", In Vivo, 20: 221-228 (2006).

Sarker et al., "Indole-e-Carbinol and prostate cancer", J of Nutrition, pp. 2493S-3498S (2004).

Weng et al., "A potent indole-3-crbinol-derived antitumor agent with pleiotropic effects on multiple signaling pathways in prostate cancer cells", Cancer Research, US, vol. 67, No. 16, pp. 7815-7824, Aug. 15, 2007.

Zhang et al., "Indole-3-carbinol induces a G1 cell cycle arrest and inhibits prostate-specific antigen production in human LNCaP prostate carcinoma cells", Cancer 98: 2511-2520 (2003).

International Search Report and Written Opinion from PCT/US10/46578 dated Oct. 1, 2010.

Amendment from U.S. Appl. No. 12/118,591 dated Jan. 19, 2010.

Notice of Allowance from U.S. Appl. No. 12/118,591 dated May 28, 2010.

Golub et al., "Molecular Classification of Cancer: Class Discovery and Class Prediction by Gene Expression Monitoring", Science, vol. 286, pp. 521-537, Oct. 15, 1999.

Lala et al., "Role of nitric oxide in tumor progression: Lessons from Experimental tumors", Cancer and Metastasis Reviews, 17 (1), pp. 91-116 (1998).

* cited by examiner

H. Prostate cancer cell lines

I. Breast cancer cell lines

ALKYL INDOLE-3-CARBINOL-DERIVED ANTITUMOR AGENTS

STATEMENT REGARDING FEDERALLY FUNDED RESEARCH

This invention was made with government support under CA112250 and CA135560, both awarded by the National Cancer Institute. The government has certain rights in the invention.

BACKGROUND OF THE INVENTION

The chemopreventive potential of indole-3-carbinol, a naturally occurring phytochemical in cruciferous vegetables, has received much attention in light of its demonstrated in vivo efficacy to protect against chemical-induced carcinogenesis in animals. Moreover, the clinical benefits of indole-3-carbionol have also been demonstrated in human trials for cervical dysplasia, breast cancer, and vulvar intraepithelial neoplasia. Despite these advances in translational research, the mechanism by which indole-3-carbinol inhibits tumorigenesis remains inconclusive, which, in part, might be attributable to its metabolic instability and complicated pharmacological properties. The intrinsic instability of indole-3-carbinol in acidic milieu arises from the vinyl hemiaminal moiety of the indole ring. This unique structural feature underlies the high susceptibility of indole-3-carbinol to acid-catalyzed dehydration and condensation to generate a complicated series of oligomeric products in vivo, including DIM (3,3'-diindoylmethane), ICZ (indolo[3,2b]-carbazole), $LTr_1$ (a linear trimer), CTr (a cyclic trimer), and CTet (a cyclic tetramer). Similar to indole-3-carbinol, all these metabolites exhibit inhibitory activities against tumor cell growth, albeit with moderate to low potency.

Mechanistic evidence indicates that indole-3-carbinol facilitates growth arrest and apoptosis by targeting a broad range of signaling pathways pertinent to cell cycle regulation and survival, including those mediated by Akt, NF-κB, Bcl-2, mitogen-activated protein (MAP) kinases, the cyclin-dependent kinase (CDK) inhibitors p21 and p27, and cyclin D1. However, as these signaling targets often operate in a cell-specific fashion, it remains in dispute whether any of them could solely account for the effect of indole-3-carbinol on growth arrest and apoptosis in tumor cells. Furthermore, indole-3-carbinol and its metabolites suffer from metabolic instability, unpredictable pharmacokinetic properties, and low in vitro antiproliferative potency, which render therapeutic concentrations difficult to predict in the body.

Recent years have witnessed the use of DIM as a scaffold to carry out structural modifications, which has led to three distinct antitumor agents with higher potency: (p-substituted phenyl)-DIMS (PPARγ agonists), SR13668 (an Akt inhibitor), and an indole-3-carbinol tetrameric derivative (a CDK6 inhibitor). These agents exhibit μM potency in inducing apoptosis or cell cycle arrest. However, they operate through signaling pathways distinct from those affected by DIM.

The use of indole-3-carbinol as a scaffold has previously been investigated as described in U.S. Patent Publication No. 2008/0300291 by Chen et al, the disclosure of which is incorporated herein by reference. In this previous work, Chen et al. described a series of pleiotropic anticancer agents that retained the broad spectrum antitumor activity of the parent compound while exhibiting enhanced metabolic stability and higher potency in various types of cancer. However, the need remains for additional antitumor compounds based on the indole-3-carbinol scaffold, and in particular for compounds exhibiting higher potency relative to previously identified compounds.

SUMMARY OF THE INVENTION

The invention relates to novel indole-3-carbinol-derived antitumor agents that are structurally and mechanistically distinct from known derivates generated from indole-3-carbinol. Because these compounds bear at least one alkyl group on phenyl portion of the indole ring, they may be referred to herein as alkyl indole-3-carbinol derivatives. The compounds of the present invention are shown in formula I:

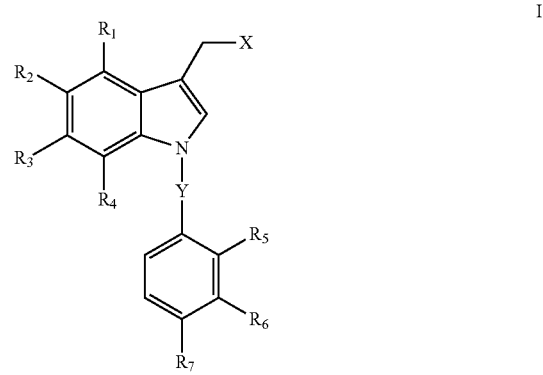

wherein X is hydroxyl, thiol, or amino; Y is carboxyl or sulfonyl; $R_1$, $R_2$, $R_3$, and $R_4$ can be the same or different and are either hydrogen and lower alkyl; and $R_5$, $R_6$, and $R_7$ may be the same or different and are selected from hydrogen, halo, nitro, amino, and methoxy.

In one embodiment, the invention provides a method of inducing apoptosis in proliferating cells that includes the step of contacting the proliferating cells with a therapeutically effective amount of a compound of formula I, as defined above. As with previous indole-3-carbinol-derivatives developed by the inventors, the alkyl indole-3-carbinol derivatives exhibit the ability to target multiple molecular defects clinically relevant to oncogenesis and tumor progression, thereby providing an effective strategy for cancer therapy. Accordingly, another embodiment of the invention provides a method of treating or preventing cancer in a subject that includes administering a therapeutically effective amount of a compound of formula I, as defined above, to the subjects. As demonstrated by the data provided herein, the alkyl indole-3-carbinol derivatives can treat a variety of different cancers, including but not limited to prostate cancer, breast cancer, leukemia, non-small cell lung cancer, colon cancer, CNS cancer, melanoma, ovarian cancer, and renal cancer.

DETAILED DESCRIPTION OF THE INVENTION

Figure 1:
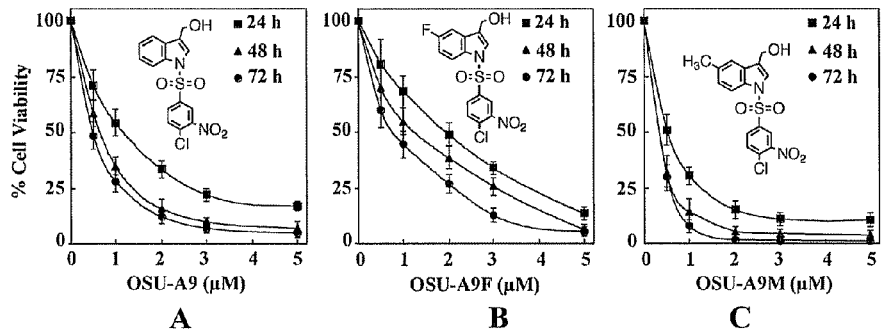
FIG. 1 provides three graphs (A-C) showing the in vitro potency of OSU-A9M (C) versus OSU-A9 (A) and OSU-A9F (B) in suppressing PC-3 cell viability in 10% FBS-supplemented RPMI 1640 medium at 24, 48, and 72 h by MTT assays. Each data point represents means±S.D. (n=6).

Described herein are compounds of formula I:

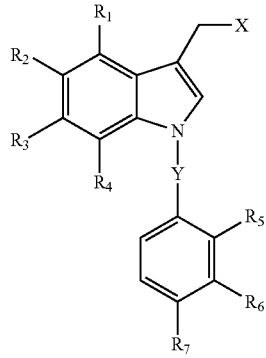

I wherein X is hydroxyl, thiol, or amino; Y is carboxyl or sulfonyl; $R_1$, $R_2$, $R_3$, and $R_4$ can be the same or different and are either hydrogen and lower alkyl; and $R_5$, $R_6$, and $R_7$ may be the same or different and are selected from hydrogen, halo, nitro, amino, and methoxy. Also included are pharmaceutically acceptable salts of these compounds.

In certain embodiments of the compound of formula I, X is hydroxyl. In other embodiments, Y is sulfonyl. In further embodiments, X is hydroxyl and Y is sulfonyl. In additional embodiments, $R_1$, $R_2$, $R_3$, and $R_4$ are selected from hydrogen, methyl, and combinations thereof. In yet further embodiments, one of $R_1$, $R_2$, $R_3$, and $R_4$ is methyl and the remainder of $R_1$, $R_2$, $R_3$, and $R_4$ are hydrogen.

In certain additional embodiments of the compound of formula I, $R_5$, $R_6$, and $R_7$ are selected from hydrogen, chloro, nitro, and combinations thereof. In particular aspects of these embodiments, $R_5$ is hydrogen, $R_6$ is nitro, and $R_7$ is chloro.

In other embodiments, the compound of formula I is selected from [1-(4-chloro-3-nitro-benzenesulfonyl)-5-methyl-1H-indol-3-yl]-methanol (OSU-A9M)

1-(4-chloro-3-nitro-benzenesulfonyl)-4-methyl-1H-indol-3-yl]-methanol

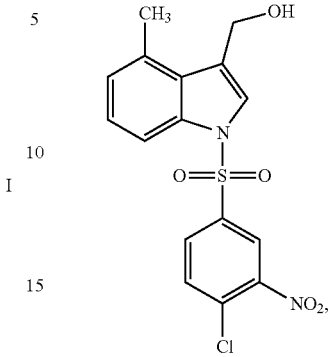

1-(4-chloro-3-nitro-benzenesulfonyl)-6-methyl-1H-indol-3-yl]-methanol

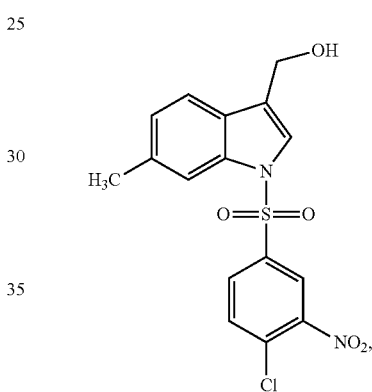

and
1-(4-chloro-3-nitro-benzenesulfonyl)-7-methyl-1H-indol-3-yl]-methanol

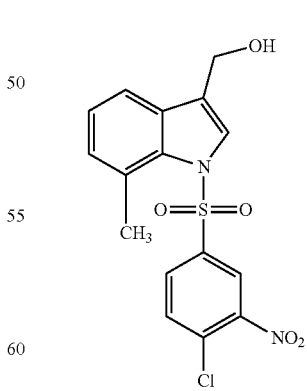

and pharmaceutically acceptable salts thereof.

In a further embodiment, the compound of formula I is the compound [1-(4-chloro-3-nitro-benzenesulfonyl)-5-methyl-1H-indol-3-yl]-methanol (OSU-A9M)

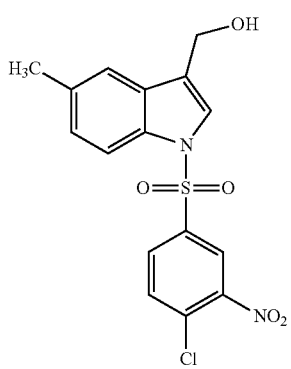

and pharmaceutically acceptable salts thereof.

The compounds of formula I, including specific embodiments thereof, are useful in inducing apoptosis in proliferative cells such as cancer cells. The compounds are further useful for treating, preventing, and delaying the onset of cancer in mammals, and especially in humans. Cancers that these compounds work particularly well against include, but are not limited to prostate cancer, breast cancer, leukemia, non-small cell lung cancer, colon cancer, CNS cancer, melanoma, ovarian cancer, and renal cancer. Surprisingly, the compounds of the present invention are able to induce apoptosis in cancer cells independent of the level of Bcl-2 expression and p53 functional status, which means that the inventive compounds are potent even against cancers that are androgen-independent, such as hormone-refractory prostate cancer.

Also provided are methods of using the compounds of formula I to treat, to prevent, or to delay the onset of disorders characterized by unwanted, rapid cell proliferation, including but not limited to cancer. The methods can include inducing apoptosis in undesirable rapidly proliferating cells. The methods comprise administering a therapeutically effective amount of a compound of formula I to a subject having a disorder or being predisposed to a disorder involving proliferating cells. The present invention also relates methods of using the inventive compounds to treat specific kinds of cancers, including but not limited to prostate cancer, breast cancer, leukemia, non-small cell lung cancer, colon cancer, CNS cancer, melanoma, ovarian cancer, and renal cancer. Further provided are methods of treating, preventing, and delaying the onset of androgen-independent cancers, including methods of treating advanced prostate cancer.

The compounds and methods described herein are useful for, but not limited to treating, preventing, or delaying the onset of cancers. The compounds and methods are also useful in the treatment of precancers (e.g., nonmalignant dysplasia) and other incidents of undesirable cell proliferation. The compounds of formula I may be administered to a subject experiencing undesirable cell proliferation. Undesirable cell proliferation typically represents cell proliferation that occurs as part of a known pathology, as opposed to the cell proliferation that occurs in a healthy individual such as the ongoing replacement of skin or gut tissue. Furthermore, the alkyl indole-3-carbinol derivatives of the invention are useful in the prevention of the development of cancers in individuals with precancers, as well as individuals prone to these disorders by administration of the compounds of formula I to these individuals.

The term "treatment" as used herein includes the partial or total destruction of at least a significant portion of undesired proliferating cells with tolerable destructive effects on normal cells. At the cellular level, treatment may result in apoptosis of the proliferating cells.

The term "preventing" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells, or arresting or reversing the progression of cancer cells into more malignant forms. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence, while avoiding adverse side effects typically associated with alternative therapies.

The term "subject" for purposes of treatment includes any human or animal subject who has a disorder characterized by unwanted, rapid cell proliferation or is at risk of developing such a disorder. Such disorders include, but are not limited to cancers and precancers. For methods described herein, the subject is any human or animal subject, and in some embodiments, the subject is a human subject who has developed or is at risk of developing a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs.

The compounds of the present invention may trigger cell death by a number of different mechanisms. However, a particular aspect of many of the inventive compounds is their ability to induce apoptosis in proliferative cells, and particularly unwanted, proliferative cells. The term "apoptosis" refers to the process of programmed cell death. In every person hundreds of thousands of old or damaged cells die each day by the process of apoptosis and are replaced in the ebb and flow of maintaining a constant number of living cells in the body. Old and damaged cells die in response to a signal triggered on the cell surface for the targeted cell to self destruct. Apoptosis is distinguished from other mechanisms of cell death, such as necrosis, which results in inflammation including swelling, redness, pain and tenderness. Apoptosis does not stimulate such reactions. In apoptosis, the cells shrivel up, break into pieces and the contents are quietly removed by methods that do not induce inflammation. For these reasons, it is highly desirable to induce apoptosis, rather than necrosis, in rapidly proliferating cells, such as cancer cells. However, mutations in some cancer cells confer resistance of these cells to apoptosis. The compounds described herein have been found to induce apoptosis even in cancer cells which, because of mutations, are otherwise resistant to apoptosis. Apoptosis can be distinguished from other treatment mechanisms by methods such as microscopy, using methods known in the art.

The terms "proliferative cells," "proliferating cells," "rapidly proliferating cells," "undesirable proliferating cells," "undesirable rapidly proliferating cells," "unwanted rapidly proliferating cells," and the like, refer to cancer cells, precancer cells, and other cells dividing at an undesirable rate in a subject. As these proliferating cells are typically part of a pathological process, they can also be referred to as pathologically proliferating cells.

Derivatives are intended to encompass any compounds which are structurally related to the compounds of formula I which possess the substantially equivalent activity, as measured by the derivative's ability to induce apoptosis in rapidly proliferating cells without substantial COX-2 inhibition. By way of example, such compounds may include, but are not limited to, prodrugs thereof.

Metabolites are intended to encompass compounds that are structurally related to the compounds of formula I and which can be formed in vivo, such as by metabolic mechanisms. Active metabolites are those which possess substantially equivalent activity to the parent compound. For example, indole-3-carbinol compounds are susceptible to acid-catalyzed dehydration and condensation to generate a complicated series of oligomeric products in vivo.

Where the turn alkyl is used, either alone or with other terms, such as haloalkyl or alkylaryl, it includes $C_1$ to $C_{10}$ linear or branched alkyl radicals, examples include methyl, ethyl, propyl, isopropyl, butyl, tert-butyl, and so forth. When the term lower alkyl is used, it includes $C_1$ to $C_4$ linear or branched alkyl radicals. The term "haloalkyl" includes $C_1$ to $C_{10}$ linear or branched alkyl radicals substituted with one or more halo radicals. Some examples of haloalkyl radicals include trifluoromethyl, 1,2-dichloroethyl, 3-bromopropyl, and so forth. The term "halo" includes halogen radicals selected from F, Cl, Br, and I. Alkyl radical substituents of the present invention may also be substituted with other groups such as azido, for example, azidomethyl, 2-azidoethyl, 3-azidopropyl and so on. Carboxyl and sulfonyl, as used herein to define the substituent Y, refer to divalent molecules with the structure O=C=O or O=S=O, respectively.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl and so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth. "Haloaryl" refers to aryl radicals in which one or more substitutable positions has been substituted with a halo radical, examples include fluorophenyl, 4 chlorophenyl, 2,5 chlorophenyl and so forth.

The compounds of formula I are often provides as pharmaceutically acceptable salts. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of formula I may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, galactaric, and galacturonic acids. Suitable pharmaceutically acceptable base addition salts of compounds of formula I include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds of formula I. All of these salts may be prepared by conventional means from the corresponding compounds of formula I by reacting, for example, the appropriate acid or base with the compound of formula I.

The present invention further embodies a pharmaceutical composition for inducing apoptosis in undesirable, rapidly proliferating cells, such as for treating, preventing, or delaying the onset of a cancer in a subject in need of such treatment. The pharmaceutical composition comprises a therapeutically effective amount of a compound of formula I or a derivative or pharmaceutically acceptable salt thereof, in association with at least one pharmaceutically acceptable carrier, adjuvant, or diluent (collectively referred to herein as "carrier materials") and, if desired, other active ingredients. The active compounds of the present invention may be administered by any suitable route known to those skilled in the art, in the form of a pharmaceutical composition adapted to such a route, and in a dose effective for the treatment intended. The active compounds and composition may, for example, be administered orally, intra-vascularly, intraperitoneally, intranasally, intrabronchially, subcutaneously, intramuscularly or topically (including aerosol). With some subjects local administration, rather than system administration, may be more appropriate. Formulation in a lipid vehicle may be used to enhance bioavailability.

The administration of the present invention may be for either prevention or treatment purposes. The methods and compositions used herein may be used alone or in conjunction with additional therapies known to those skilled in the art in the prevention or treatment of disorders characterized by unwanted, rapid proliferation of cells. Alternatively, the methods and compositions described herein may be used as adjunct therapy. By way of example, the apoptosis-inducing compounds of the present invention may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for use together with the compounds of formula I for the treatment of cancers or other disorders characterized by rapid proliferation of cells to provide combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors (MMP), such as MMP-13 inhibitors including batiastat, marimastat, Agouron Pharmaceuticals AG-3340, and Roche RO-32-3555, or $\alpha_v\beta_3$ inhibitors may be used. Suitable agents which may be used in combination therapy will be recognized by those of skill in the art. Similarly, when combination therapy is desired, radioprotective agents known to those of skill in the art may also be used.

The phrase "adjunct therapy" (or "combination therapy"), in defining use of a compound of the present invention and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

For oral administration, the pharmaceutical composition may be in the form of, for example, a tablet, capsule, suspension or liquid. In some embodiments, the pharmaceutical composition is made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is, in some embodiments, isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

If the unwanted proliferating cells are localized in the G.I. tract, the compound may be formulated with acid-stable, base-labile coatings known in the art which begin to dissolve in the high pH small intestine. In some exemplary embodiments, the compound is formulated to enhance local pharmacologic effects and reduce systemic uptake.

Formulations suitable for parenteral administration conveniently comprise a sterile aqueous preparation of the active compound which, in some embodiments, isotonic. Preparations for injections may also be formulated by suspending or emulsifying the compounds in non-aqueous solvent, such as vegetable oil, synthetic aliphatic acid glycerides, esters of higher aliphatic acids or propylene glycol.

Formulations for topical use include known gels, creams, oils, and the like. For aerosol delivery, the compounds may be formulated with known aerosol excipients, such as saline, and administered using commercially available nebulizers. Formulation in a fatty acid source may be used to enhance biocompatibility.

For rectal administration, the active ingredient may be formulated into suppositories using bases which are solid at room temperature and melt or dissolve at body temperature. Commonly used bases include cocoa butter, glycerinated gelatin, hydrogenated vegetable oil, polyethylene glycols of various molecular weights, and fatty esters of polyethylene stearate.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg in some embodiments, in the range of about 0.5 to 500 mg in other embodiments, and between about 1 and 200 mg in still other embodiments. In some embodiments, a daily dose of about 0.01 to 100 mg/kg body weight is appropriate. In other embodiments, a daily dost of between about 0.1 and about 50 mg/kg body weight, may be appropriate. The daily dose can be administered in single or multiple doses per day.

EXAMPLES

The invention will be further described by reference to the following detailed examples. These examples are offered to further illustrate the various specific and preferred embodiments and techniques. It should be understood, however, that many variations and modifications may be made while remaining within the scope of the present invention.

Example I

Synthesis of OSU-A9M

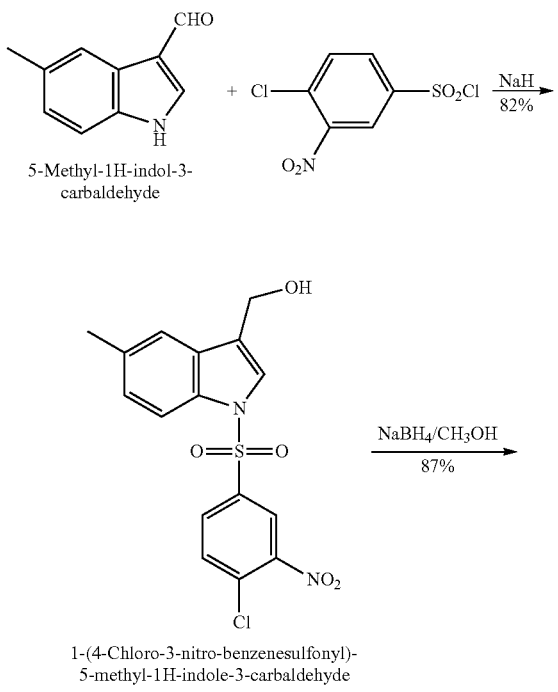

Scheme 1: Synthetic scheme of OSU-A9M

-continued

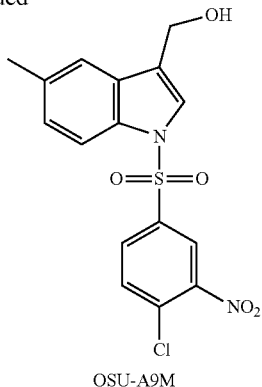

OSU-A9M

Reagents. Methyl-1H-Indole-3-carbaldehydes were used as the starting material to synthesize the methyl 1H-indole-3-carbinol derivatives (Sigma Aldrich). Other alkyl-1H indole-3-carbaldehydes can readily be used to prepare other lower alkyl derivatives. The identity and purity of these synthetic derivatives were verified by proton nuclear magnetic resonance, high-resolution mass spectrometry, and elemental analysis, and were typically present with a purity of ≧99%. For in vitro experiments, these agents were dissolved in DMSO at various concentrations and were added to cells in medium to provide a final DMSO concentration of 0.1%.

1-(4-Chloro-3-nitro-benzenesulfonyl)-5-methyl-1H-indole-3-carbaldehyde. 5-Methyl-1H-indole-3-carbaldehyde (159.18 mg, 1.0 mmol) was treated with NaH (24 mg, 1.0 mmol) in THF at 0° C. for 30 min, sulfonyl chloride (256.06 mg, 1.0 mmol) was added slowly. The reaction mixture was warmed up to and stirred at room temperature for 16 h, concentrated, and the residue was diluted with ethyl acetate, washed with water and brine, and dried over $Na_2SO_4$. Solvent was removed in vacuo and the residue was purified with column chromatography to afford pure product (311.6 mg, 82%), as light yellow solid.

[1-(4-Chloro-3-nitro-benzenesulfonyl)-5-methyl-1H-indol-3-yl]-methanol (OSUA9M). To the solution of 1-(4-chloro-3-nitro-benzenesulfonyl)-5-methyl-1H-indole-3-carbaldehyde (284.10 mg, 0.75 mmol) in the mixture of methanol/THF (1:1, 20 mL), $NaBH_4$ (32 mg, 0.825 mmol) was added slowly at 0° C. After addition, the reaction was stirred for additional 30 min at same temperature. 1.0 ml of 1N HCl was added after reaction was completed, as determined by checking using thin layer chromatography (TLC). The resulting reaction mixture was concentrated, and the residue was diluted with water (20 ml) and extracted with ethyl acetate (3×10 ml). The combined organic layers was washed with water, 10% $NaHCO_3$, and brine, dried with $MgSO_4$, filtered and concentrated. The residue was purified with column chromatography to give pure product, OSU-A9M (248.5 mg, 87%) as off white solid.

Example II

OSU-A9M Exhibits Greater In Vitro Potency than OSU-A9 and OSU-A9F in Suppressing the Cell Viability of PC-3 Cells The activity of OSU-A9M versus its parent compound A9 ([1-(3'-nitro-4'-chlorobenzenesulfonyl)-1H-indol-3-yl]-methanol) and its fluorinated counterpart OSU-A9F ([1-(4-Chloro-3-nitro-benzenesulfonyl)-5-fluoro-1H-indol-3-yl])-methanol in suppressing the cell viability of PC-3 prostate cancer cells was compared using the MTT [3-(4,5-dimethylthiazol-2-yl)-2,5-diphenyl-2H-tetrazolium bromide] assay. The results are shown in FIG. 1. Cancer cells and PrECs were grown in 5% FBS-supplemented RPMI 1640 medium or 5% FBS-supplemented prostate epithelial growth medium, respectively, in 96-well, flat-bottomed plates for 24 h, and then exposed to various concentrations of test agents in the same medium for the indicated time intervals. Controls received DMSO vehicle at a concentration equal to that in drug-treated cells. At the end of the treatment, the medium was removed, replaced by 200 µL of 0.5 mg/mL of MTT in the same medium, and cells were incubated in the $CO_2$ incubator at 37° C. for 2 h. Supernatants were removed from the wells, and the reduced MTT dye was solubilized in 200 µL/well DMSO. Absorbance at 570 nm was determined on a plate reader.

Example III

OSU-A9M Exhibits Higher Potency than OSU-A9 in Suppressing Cancer Cell Growth per the NCI 60 Cell Line Screening Analysis The National Cancer Institute carried out experiments to evaluate the anticancer activity of OSU-A9M against a variety of different cancers using various different cell lines. For a review of the NCI60 screening method, see Shoemaker, R. H., Nature Reviews, 6: p. 813-823 (2006). More specifically, OSU-A9M was tested for its ability to inhibit the growth of prostate cancer, breast cancer, leukemia, non-small cell lung cancer, colon cancer, CNS cancer, melanoma, ovarian cancer, and renal cancer cell lines. The results are shown numerically in Table I, and graphically in FIG. 4 A-I. The different cell lines used are shown in both the table and the graphs. For example, CCFR-CEM, HL-60, K-562, MOLT-4, RPMI-8226, and SR cell lines were used to evaluate the effect of OSU-A9M on leukemia. The same experiments were also carried out to evaluate the effect of OSU-A9 on these cancer cell lines (data now shown). Comparison of the data from these two experiments demonstrated that OSU-A9M exhibited significantly higher potency.

TABLE I

Log10 Concentration values for the inhibition of cancer cell lines by OSU-A9M

| Panel/Cell Line | Time | | Mean Optical Densities | | | | | Percent Growth | | | | | GI50 | TGI | LC50 |
| --- | --- | --- | --- | --- | --- | --- | --- | --- | --- | --- | --- | --- | --- | --- | --- |
| | Zero | Ctrl | -8.0 | -7.0 | -6.0 | -5.0 | -4.0 | -8.0 | -7.0 | -6.0 | -5.0 | -4.0 | | | |
| Leukemia | | | | | | | | | | | | | | | |
| CCRF-CEM | 0.548 | 2.030 | 1.800 | 1.769 | 0.762 | 0.435 | 0.264 | 84 | 82 | 14 | -21 | -52 | 3.00E-7 | 2.58E-6 | 8.74E-5 |
| HL-60(TB) | 0.746 | 1.952 | 1.845 | 1.756 | 1.582 | 0.504 | 0.248 | 91 | 84 | 69 | -32 | -67 | 1.55E-6 | 4.80E-6 | 3.25E-5 |
| K-562 | 0.268 | 1.384 | 1.366 | 1.450 | 0.838 | 0.121 | 0.080 | 98 | 106 | 51 | -55 | -70 | 1.02E-6 | 3.03E-6 | 8.96E-6 |
| MOLT-4 | 0.478 | 1.847 | 1.731 | 1.635 | 0.733 | 0.263 | 0.172 | 92 | 85 | 19 | -45 | -64 | 3.34E-7 | 1.96E-6 | 1.83E-5 |

TABLE I-continued

Log10 Concentration values for the inhibition of cancer cell lines by OSU-A9M

| Panel/Cell Line | Time Zero | Ctrl | Mean Optical Densities | | | | | Percent Growth | | | | | GI50 | TGI | LC50 |
|---|---|---|---|---|---|---|---|---|---|---|---|---|---|---|---|
| | | | -8.0 | -7.0 | -6.0 | -5.0 | -4.0 | -8.0 | -7.0 | -6.0 | -5.0 | -4.0 | | | |
| RPMI-8226 | 0.890 | 2.332 | 2.226 | 2.108 | 1.985 | 0.400 | 0.288 | 93 | 84 | 76 | -55 | -68 | 1.58E-6 | 3.80E-6 | 9.14E-6 |
| SR | 0.577 | 1.716 | 1.545 | 1.652 | 0.765 | 0.431 | 0.314 | 85 | 94 | 16 | -25 | -46 | 3.71E-7 | 2.47E-6 | >1.00E-4 |
| Non-Small Cell Lung Cancer | | | | | | | | | | | | | | | |
| A549/ATCC | 0.102 | 1.059 | 1.006 | 1.002 | 0.976 | 0.060 | 0.055 | 95 | 94 | 91 | -41 | -47 | 2.05E-6 | 4.89E-6 | >1.00E-4 |
| EKVX | 0.731 | 1.939 | 1.827 | 1.925 | 1.753 | 0.109 | 0.055 | 91 | 99 | 85 | -85 | -93 | 1.60E-6 | 3.15E-6 | 6.21E-6 |
| HOP-62 | 0.424 | 1.198 | 1.185 | 1.159 | 1.177 | -0.005 | 0.003 | 98 | 95 | 97 | -100 | -99 | 1.74E-6 | 3.11E-6 | 5.58E-6 |
| HOP-92 | 0.952 | 1.422 | 1.383 | 1.310 | 1.276 | 0.068 | 0.029 | 92 | 76 | 69 | -93 | -97 | 1.31E-6 | 2.67E-6 | 5.43E-6 |
| NCI-H226 | 0.871 | 1.767 | 1.689 | 1.704 | 1.311 | 0.478 | 0.301 | 91 | 93 | 49 | -45 | -65 | 9.53E-7 | 3.32E-6 | 1.74E-5 |
| NCI-H23 | 0.348 | 0.878 | 0.836 | 0.826 | 0.788 | 0.009 | 0.016 | 92 | 90 | 83 | -97 | -96 | 1.53E-6 | 2.89E-6 | 5.46E-6 |
| NCI-H322M | 0.584 | 1.532 | 1.451 | 1.429 | 1.462 | 0.025 | 0.042 | 91 | 89 | 93 | -96 | -93 | 1.68E-6 | 3.10E-6 | 5.71E-6 |
| NCI-H460 | 0.152 | 1.307 | 1.259 | 1.301 | 1.304 | 0.016 | 0.017 | 96 | 99 | 100 | -89 | -89 | 1.83E-6 | 3.36E-6 | 6.18E-6 |
| NCI-H522 | 0.302 | 0.588 | 0.523 | 0.505 | 0.126 | 0.013 | 0.012 | 77 | 71 | -58 | -96 | -96 | 1.45E-7 | 3.54E-7 | 8.61E-7 |
| Colon Cancer | | | | | | | | | | | | | | | |
| COLO 205 | 0.385 | 1.293 | 1.279 | 1.223 | 1.232 | 0.021 | 0.050 | 98 | 92 | 93 | -95 | -87 | 1.70E-6 | 3.14E-6 | 5.79E-6 |
| HCC-2998 | 0.798 | 1.607 | 1.574 | 1.533 | 1.421 | 0.002 | 0.005 | 96 | 91 | 77 | -100 | -99 | 1.42E-6 | 2.73E-6 | 5.23E-6 |
| HCT-116 | 0.130 | 0.802 | 0.809 | 0.805 | 0.295 | -0.004 | -0.005 | 101 | 100 | 24 | -100 | -100 | 4.61E-7 | 1.57E-6 | 3.97E-6 |
| HCT-15 | 0.286 | 1.267 | 1.193 | 1.211 | 1.090 | -0.006 | -0.013 | 92 | 94 | 82 | -100 | -100 | 1.50E-6 | 2.82E-6 | 5.31E-6 |
| HT29 | 0.119 | 0.816 | 0.756 | 0.772 | 0.294 | -0.034 | -0.029 | 91 | 94 | 25 | -100 | -100 | 4.34E-7 | 1.59E-6 | 3.98E-6 |
| KM12 | 0.381 | 1.538 | 1.591 | 1.505 | 1.420 | -0.007 | -0.012 | 105 | 97 | 90 | -100 | -100 | 1.62E-6 | 2.97E-6 | 5.45E-6 |
| SW-620 | 0.224 | 1.097 | 1.064 | 1.011 | 0.777 | -0.010 | 0.001 | 96 | 90 | 63 | -100 | -100 | 1.21E-6 | 2.44E-6 | 4.94E-6 |
| CNS Cancer | | | | | | | | | | | | | | | |
| SF-268 | 0.367 | 1.099 | 0.995 | 1.022 | 1.039 | -0.003 | -0.007 | 86 | 89 | 92 | -100 | -100 | 1.65E-6 | 3.01E-6 | 5.49E-6 |
| SF-295 | 0.787 | 2.656 | 2.220 | 2.482 | 2.429 | 0.059 | 0.110 | 77 | 91 | 88 | -93 | -86 | 1.62E-6 | 3.07E-6 | 5.81E-6 |
| SF-539 | 0.236 | 0.986 | 0.934 | 0.943 | 0.898 | -0.020 | -0.014 | 93 | 94 | 88 | -100 | -100 | 1.60E-6 | 2.94E-6 | 5.42E-6 |
| SNB-19 | 0.485 | 1.091 | 1.016 | 1.006 | 1.029 | -0.018 | -0.019 | 88 | 86 | 90 | -100 | -100 | 1.62E-6 | 2.97E-6 | 5.45E-6 |
| SNB-75 | 0.678 | 1.212 | 1.252 | 1.123 | 1.082 | -0.038 | -0.031 | 108 | 83 | 76 | -100 | -100 | 1.40E-6 | 2.70E-6 | 5.19E-6 |
| U251 | 0.254 | 1.140 | 1.050 | 1.022 | 1.022 | -0.031 | -0.028 | 90 | 87 | 87 | -100 | -100 | 1.57E-6 | 2.91E-6 | 5.40E-6 |
| Melanoma | | | | | | | | | | | | | | | |
| LOX IMVI | 0.112 | 0.450 | 0.397 | 0.356 | 0.016 | -0.017 | -0.025 | 84 | 72 | -86 | -100 | -100 | 1.38E-7 | 2.86E-7 | 5.94E-7 |
| MALME-3M | 0.657 | 1.276 | 1.168 | 1.139 | 1.214 | 0.285 | 0.166 | 83 | 78 | 90 | -57 | -75 | 1.87E-6 | 4.10E-6 | 9.00E-6 |
| M14 | 0.449 | 1.245 | 1.205 | 1.218 | 1.111 | 0.009 | 0.002 | 95 | 97 | 83 | -98 | -100 | 1.52E-6 | 2.88E-6 | 5.43E-6 |
| MDA-MB-435 | 0.493 | 1.950 | 1.881 | 1.761 | 1.691 | 0.031 | 0.039 | 95 | 87 | 82 | -94 | -92 | 1.52E-6 | 2.93E-6 | 5.64E-6 |
| SK-MEL-2 | 0.610 | 1.616 | 1.638 | 1.580 | 1.480 | 0.045 | 0.045 | 102 | 96 | 86 | -93 | -93 | 1.60E-6 | 3.04E-6 | 5.78E-6 |
| SK-MEL-28 | 0.401 | 0.956 | 0.915 | 0.897 | 0.883 | -0.020 | -0.022 | 93 | 89 | 87 | -100 | -100 | 1.57E-6 | 2.91E-6 | 5.40E-6 |
| SK-MEL-5 | 0.374 | 2.054 | 1.981 | 1.928 | 1.755 | -0.002 | -0.007 | 96 | 92 | 82 | -100 | -100 | 1.50E-6 | 2.83E-6 | 5.32E-6 |
| UACC-257 | 0.375 | 1.548 | 1.501 | 1.482 | 1.443 | 0.061 | 0.015 | 96 | 94 | 91 | -84 | -96 | 1.72E-6 | 3.31E-6 | 6.40E-6 |
| UACC-62 | 0.636 | 1.918 | 1.829 | 1.805 | 1.789 | 0.072 | 0.046 | 93 | 91 | 90 | -89 | -93 | 1.67E-6 | 3.19E-6 | 6.07E-6 |
| Ovarian Cancer | | | | | | | | | | | | | | | |
| IGROV1 | 0.164 | 0.487 | 0.444 | 0.481 | 0.196 | -0.032 | -0.009 | 86 | 98 | 10 | -100 | -100 | 3.49E-7 | 1.23E-6 | 3.50E-6 |
| OVCAR-3 | 0.169 | 0.485 | 0.485 | 0.492 | 0.092 | -0.013 | -0.020 | 100 | 102 | -46 | -100 | -100 | 2.25E-7 | 4.90E-7 | 1.19E-6 |
| OVCAR-5 | 0.309 | 0.889 | 0.859 | 0.845 | 0.851 | -0.013 | -0.014 | 95 | 92 | 93 | -100 | -100 | 1.68E-6 | 3.04E-6 | 5.51E-6 |
| OVCAR-8 | 0.210 | 1.398 | 1.365 | 1.406 | 1.350 | 0.074 | 0.034 | 97 | 101 | 96 | -65 | -84 | 1.93E-6 | 3.95E-6 | 8.09E-6 |
| NCI/ADR-RES | 0.367 | 1.079 | 1.048 | 1.092 | 1.070 | 0.034 | 0.028 | 96 | 102 | 99 | -91 | -93 | 1.81E-6 | 3.32E-6 | 6.09E-6 |
| SK-OV-3 | 0.442 | 1.055 | 1.026 | 1.034 | 1.006 | 0.012 | -0.013 | 95 | 97 | 92 | -97 | -100 | 1.67E-6 | 3.06E-6 | 5.62E-6 |
| Renal Cancer | | | | | | | | | | | | | | | |
| 786-0 | 0.520 | 1.643 | 1.593 | 1.619 | 1.625 | 0.024 | -0.005 | 96 | 98 | 98 | -95 | -100 | 1.78E-6 | 3.22E-6 | 5.83E-6 |
| A498 | 0.829 | 1.180 | 1.094 | 1.049 | 1.072 | 0.118 | -0.025 | 75 | 62 | 69 | -86 | -100 | 1.33E-6 | 2.79E-6 | 5.87E-6 |
| ACHN | 0.268 | 1.030 | 1.015 | 0.980 | 1.021 | -0.031 | -0.027 | 98 | 93 | 99 | -100 | -100 | 1.76E-6 | 3.14E-6 | 5.60E-6 |
| CAKI-1 | 0.551 | 1.864 | 1.759 | 1.796 | 1.588 | 0.046 | 0.028 | 92 | 95 | 79 | -92 | -95 | 1.48E-6 | 2.90E-6 | 5.70E-6 |
| RXF 393 | 0.370 | 1.579 | 1.589 | 1.608 | 1.512 | 0.149 | 0.056 | 101 | 102 | 94 | -60 | -85 | 1.94E-6 | 4.10E-6 | 8.65E-6 |
| SN12C | 0.528 | 1.398 | 1.116 | 1.332 | 1.163 | 0.102 | 0.066 | 68 | 92 | 73 | -81 | -88 | 1.41E-6 | 2.99E-6 | 6.31E-6 |
| TK-10 | 0.590 | 1.227 | 1.163 | 1.117 | 1.125 | 0.041 | 0.066 | 90 | 83 | 84 | -93 | -89 | 1.56E-6 | 2.98E-6 | 5.71E-6 |
| U0-31 | 0.478 | 1.430 | 1.310 | 1.413 | 1.405 | 0.080 | -0.017 | 87 | 98 | 97 | -83 | -100 | 1.83E-6 | 3.46E-6 | 6.54E-6 |
| Prostate Cancer | | | | | | | | | | | | | | | |
| PC-3 | 0.586 | 1.102 | 1.000 | 0.970 | 0.971 | 0.335 | 0.041 | 80 | 74 | 75 | -43 | -93 | 1.62E-6 | 4.32E-6 | 1.39E-5 |
| DU-145 | 0.317 | 1.056 | 1.078 | 1.018 | 1.006 | -0.024 | -0.027 | 103 | 95 | 93 | -100 | -100 | 1.67E-6 | 3.04E-6 | 5.51E-6 |
| Breast Cancer | | | | | | | | | | | | | | | |
| MCF7 | 0.222 | 1.313 | 1.144 | 1.149 | 0.651 | 0.057 | 0.040 | 84 | 85 | 39 | -75 | -82 | 5.82E-7 | 2.21E-6 | 6.09E-6 |
| MDA-MB-231/ATCC | 0.237 | 0.769 | 0.761 | 0.723 | 0.636 | 0.038 | 0.052 | 98 | 91 | 75 | -84 | -78 | 1.44E-6 | 2.96E-6 | 6.10E-6 |
| HS 578T | 0.397 | 0.740 | 0.681 | 0.701 | 0.572 | 0.182 | 0.148 | 83 | 88 | 51 | -54 | -63 | 1.02E-6 | 3.05E-6 | 9.11E-6 |
| BT-549 | 1.122 | 1.909 | 1.793 | 1.803 | 1.835 | 0.090 | 0.092 | 85 | 87 | 91 | -92 | -92 | 1.67E-6 | 3.13E-6 | 5.89E-6 |
| T-47D | 0.367 | 0.688 | 0.670 | 0.664 | 0.547 | 0.129 | 0.145 | 95 | 93 | 56 | -65 | -61 | 1.12E-6 | 2.91E-6 | 7.54E-6 |
| MDA-MB-468 | 0.858 | 1.636 | 1.555 | 1.525 | 1.245 | 0.026 | 0.041 | 90 | 86 | 50 | -97 | -95 | 9.79E-7 | 2.18E-6 | 4.78E-6 |

The NIC60 screening method was carried out using the following methodology. The human tumor cell lines of the cancer screening panel were grown in RPMI 1640 medium containing 5% fetal bovine serum and 2 mM L-glutamine. The cells were then inoculated into 96 well microtiter plates in 100 μL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 h prior to addition of the indole-3-carbinol derivatives.

After 24 h, two plates of each cell line were fixed in situ with TCA, to represent a measurement of the cell population for each cell line at the time of drug addition (Tz). The indole-3-carbinol derivatives were then solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 μg/ml gentamicin. Additional four, 10-fold or ½ log serial dilutions were made to provide a total of five drug concentrations plus control. Aliquots of 100 μl of these different drug dilutions are added to the appropriate microtiter wells already containing 100 μl of medium, resulting in the required final drug concentrations.

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance was read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

$$[(Ti-Tz)/(C-Tz)] \times 100 \text{ for concentrations for which } Ti >/= Tz$$

$$[(Ti-Tz)/Tz] \times 100 \text{ for concentrations for which } Ti < Tz.$$

Three dose response parameters were calculated for each experimental agent. Growth inhibition of 50% (GI50) was calculated from $[(Ti-Tz)/(C-Tz)] \times 100=50$, which is the drug concentration resulting in a 50% reduction in the net protein increase (as measured by SRB staining) in control cells during the drug incubation. The drug concentration resulting in total growth inhibition (TGI) was calculated from Ti=Tz. The LC50 (concentration of drug resulting in a 50% reduction in the measured protein at the end of the drug treatment as compared to that at the beginning) indicating a net loss of cells following treatment is calculated from $[(Ti-Tz)/Tz] \times 100=-50$. Values were calculated for each of these three parameters if the level of activity was reached; however, if the effect is not reached or is exceeded, the value for that parameter is expressed as greater or less than the maximum or minimum concentration tested.

Example IV

OSU-A9M Exhibits a Therapeutic Advantage Relative to OSU-A9 and OSU-A9F in Suppressing PC-3 Xenograft Tumor Growth in Nude Mice Although OSU-A9 achieved significant tumor growth suppression in the PC-3 model, the suppressive effect was mild and without a dose-response relationship (FIG. 1). The in vitro potency of OSU-A9M and OSU-A9F was determined at 25 and 50 mg/kg per day to be greater than or similar to that of OSU-A9 (FIG. 2) against the viability of PC-3 cells, which warranted its parallel investigation in vivo. The efficacy studies were therefore repeated with OSU-A9M and OSU-A9F, following 42 days and 49 days treatment, respectively, versus OSU-A9 with 49-day treatment.

Figure 2:
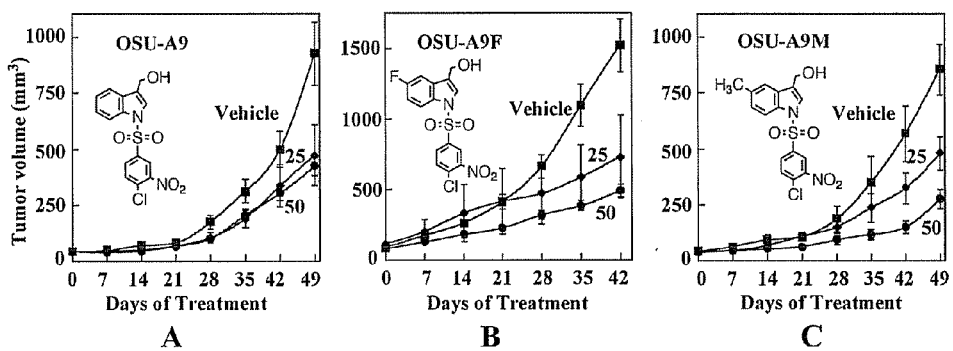
FIG. 2 provides three graphs (A-C) showing the in vivo effects of OSU-A9M (C) versus OSU-A9 (A) and OSU-A9F (B), each at 25 and 50 mg/kg per day by oral gavage, on suppressing PC-3 xenograft tumor growth in nude mice (n=6).

As shown in FIG. 2, OSU-A9M, exhibited greater potency than OSU-A9 and OSU-A9F against the viability of PC-3 cells in vitro. After 7 weeks of treatment by gavage, 25 and 50 mg/kg OSU-A9M suppressed the volume of PC-3 tumor growth by 44.0% and 67.6% (all P<0.05), respectively. In all three treatments, the body weights of drug-treated mice were not affected. No signs of overt toxicity were observed.

Example V

Figure 3:
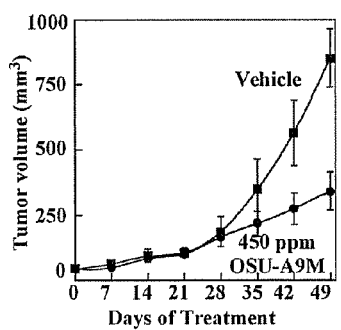
FIG. 3 provides a graph showing the in vivo efficacy of dietary OSU-A9M at 450 ppm in a rodent diet in suppressing PC-3 xenograft tumor growth in nude mice.
Figure 4A:
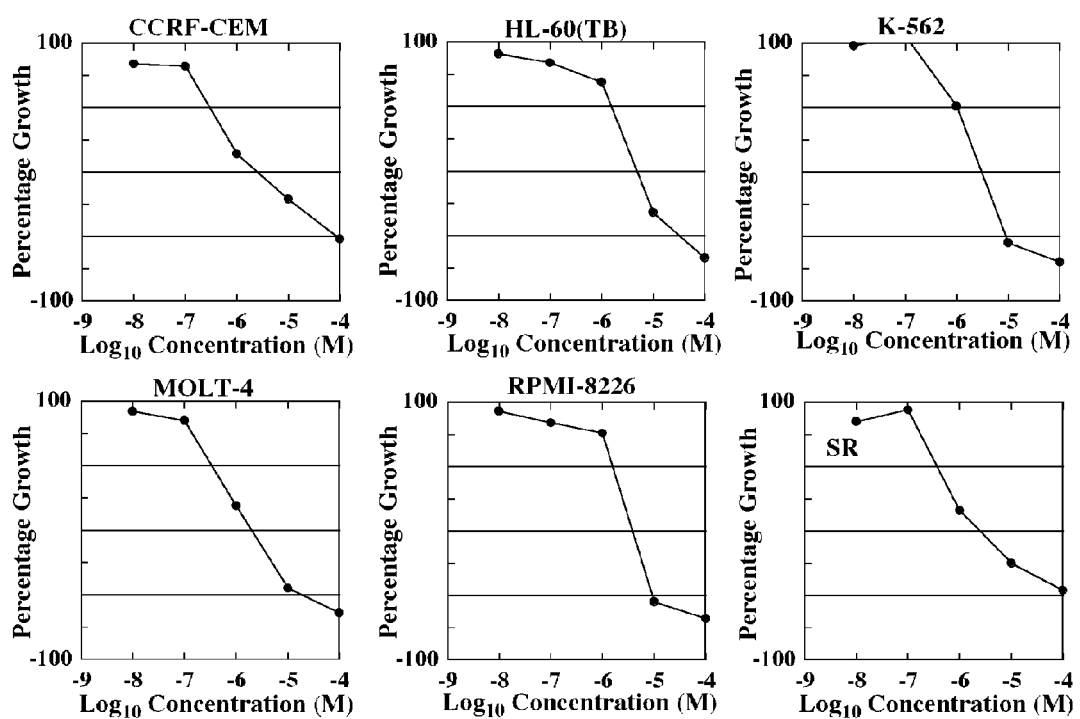
FIG. 4 provides nine graphs (A-I) showing the in vitro testing of OSU-A9M on leukemia cells (A), non-small cell lung cancer cells (B), CNS cancer cells (C), melanoma cancer cells (D), renal cancer cells (E), prostate cancer cells (F), colon cancer cells (G), ovarian cancer cells (H), and breast cancer cells (I).
Figure 4B:
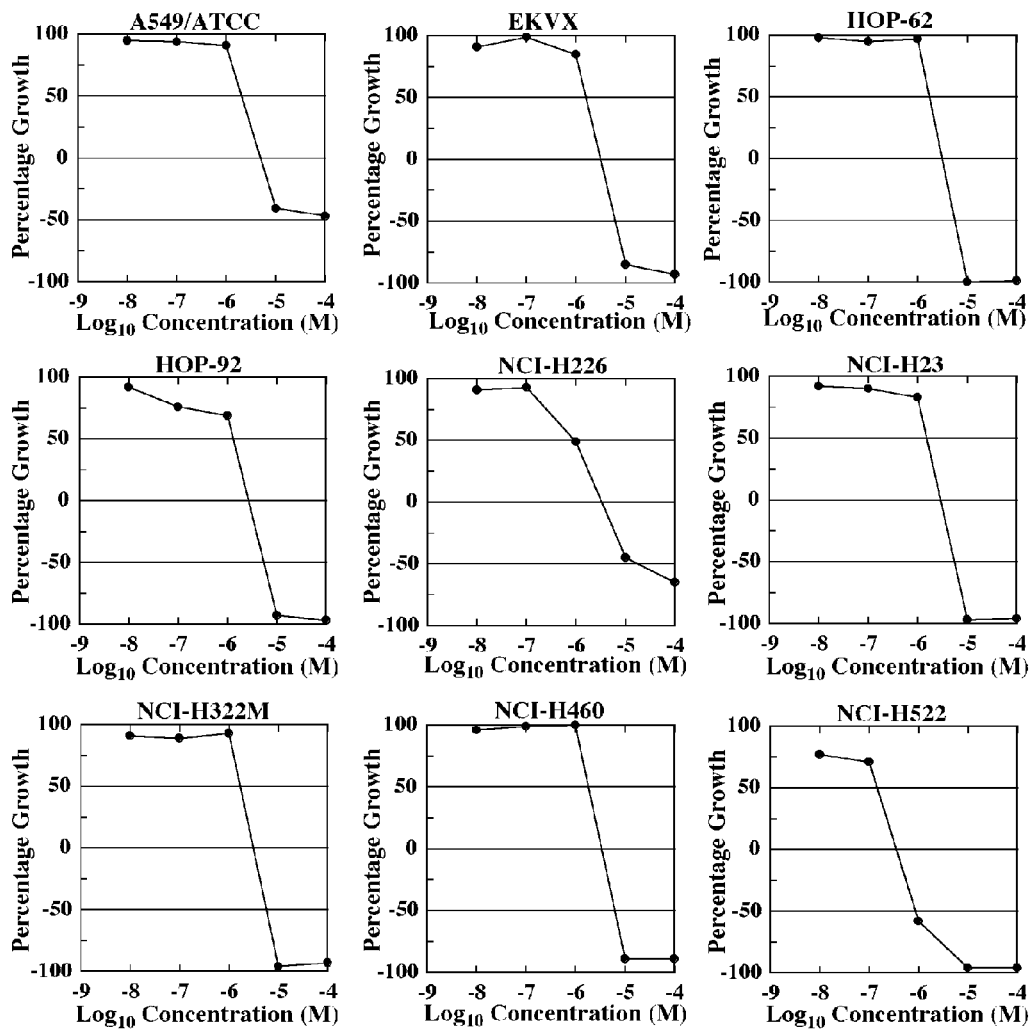
Figure 4C:
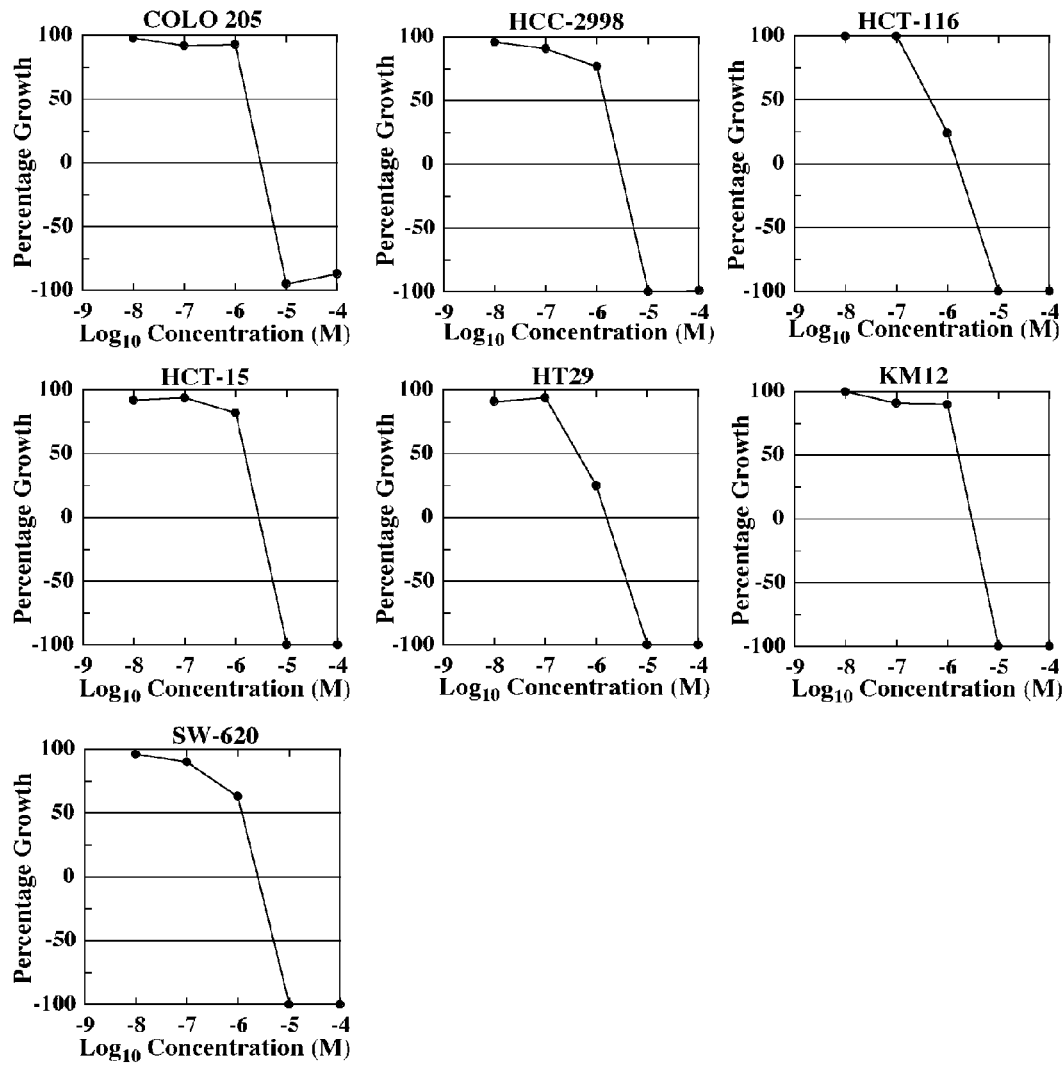
Figure 4D:
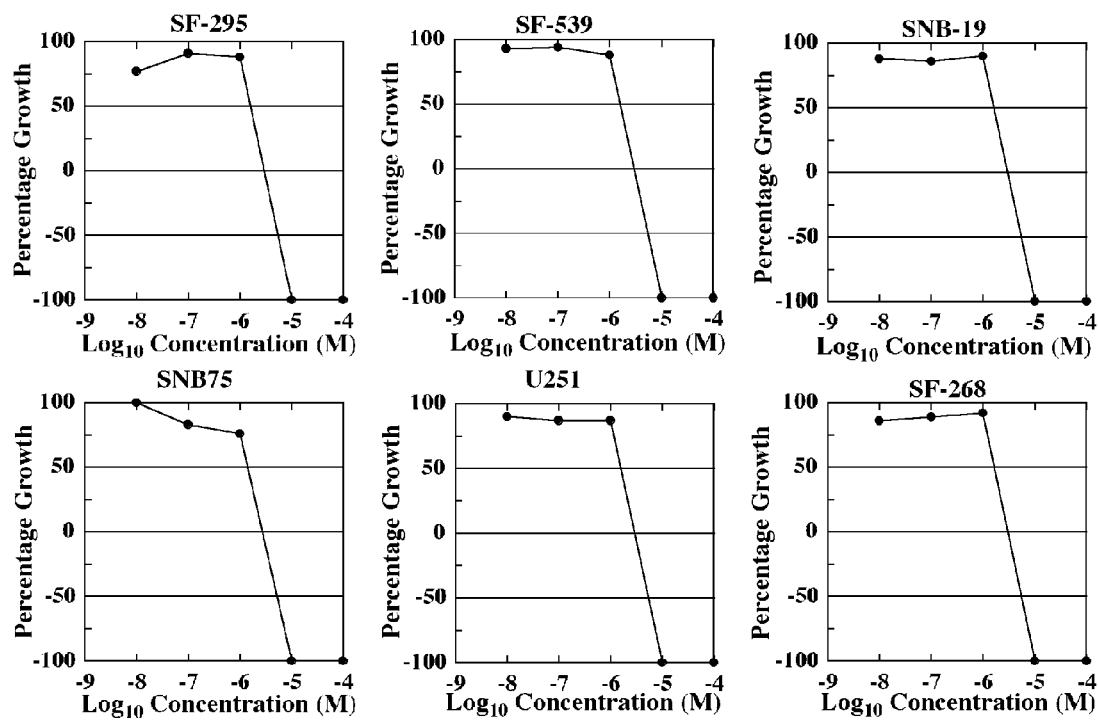
Figure 4E:
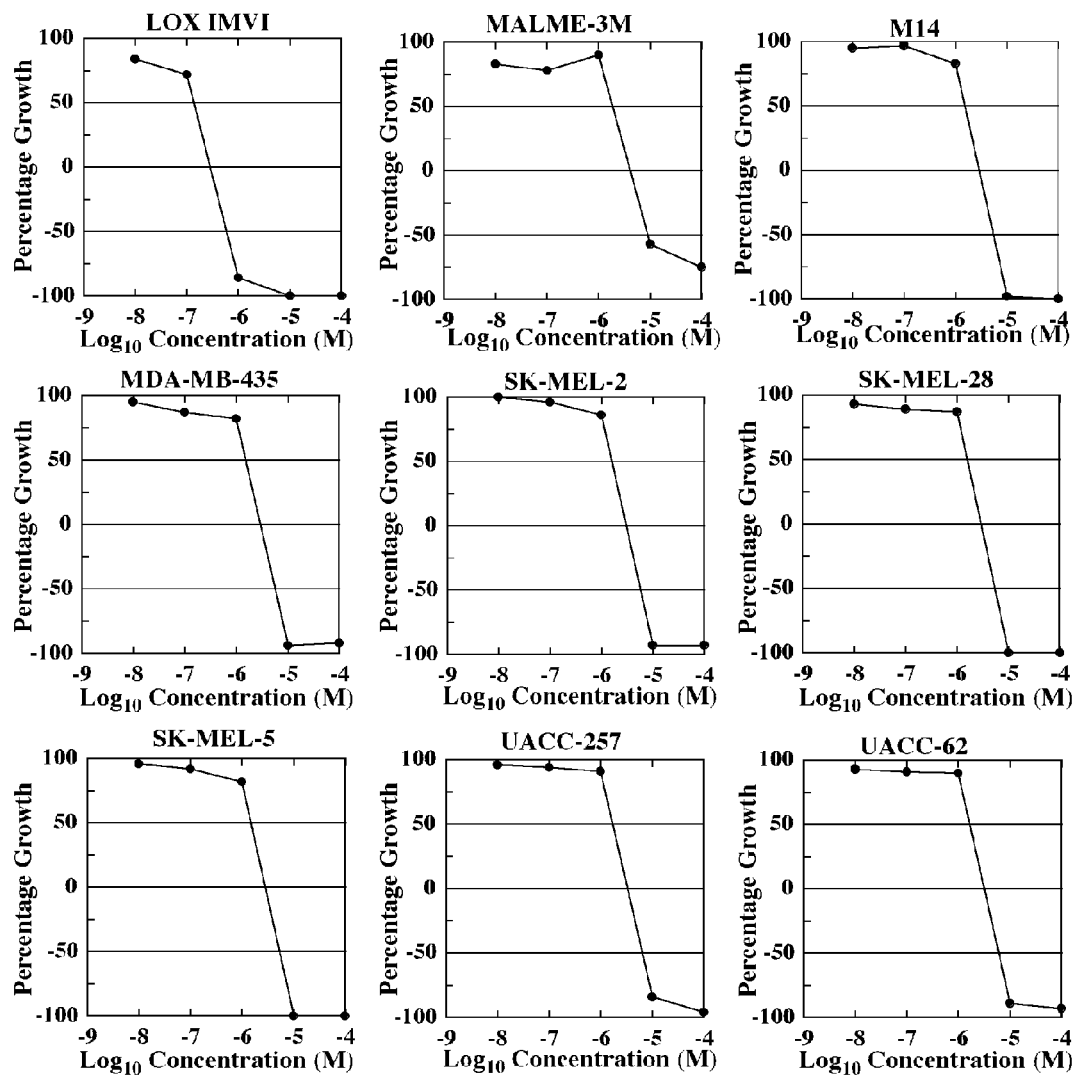
Figure 4F:
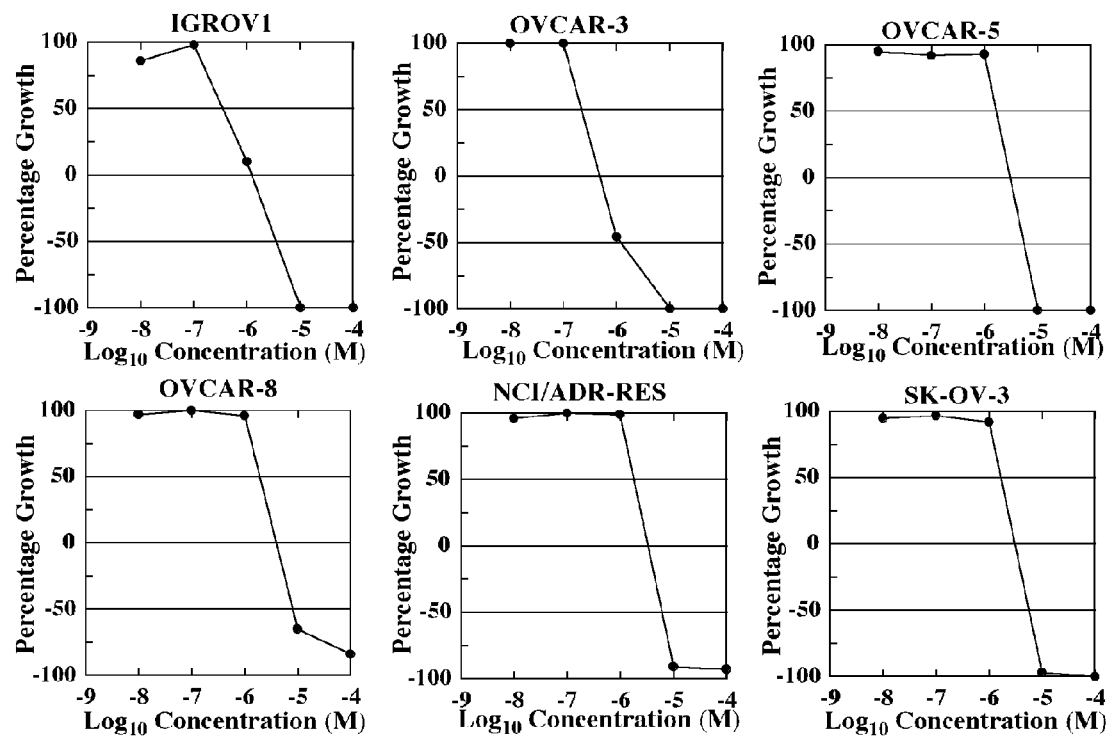
Figure 4G:
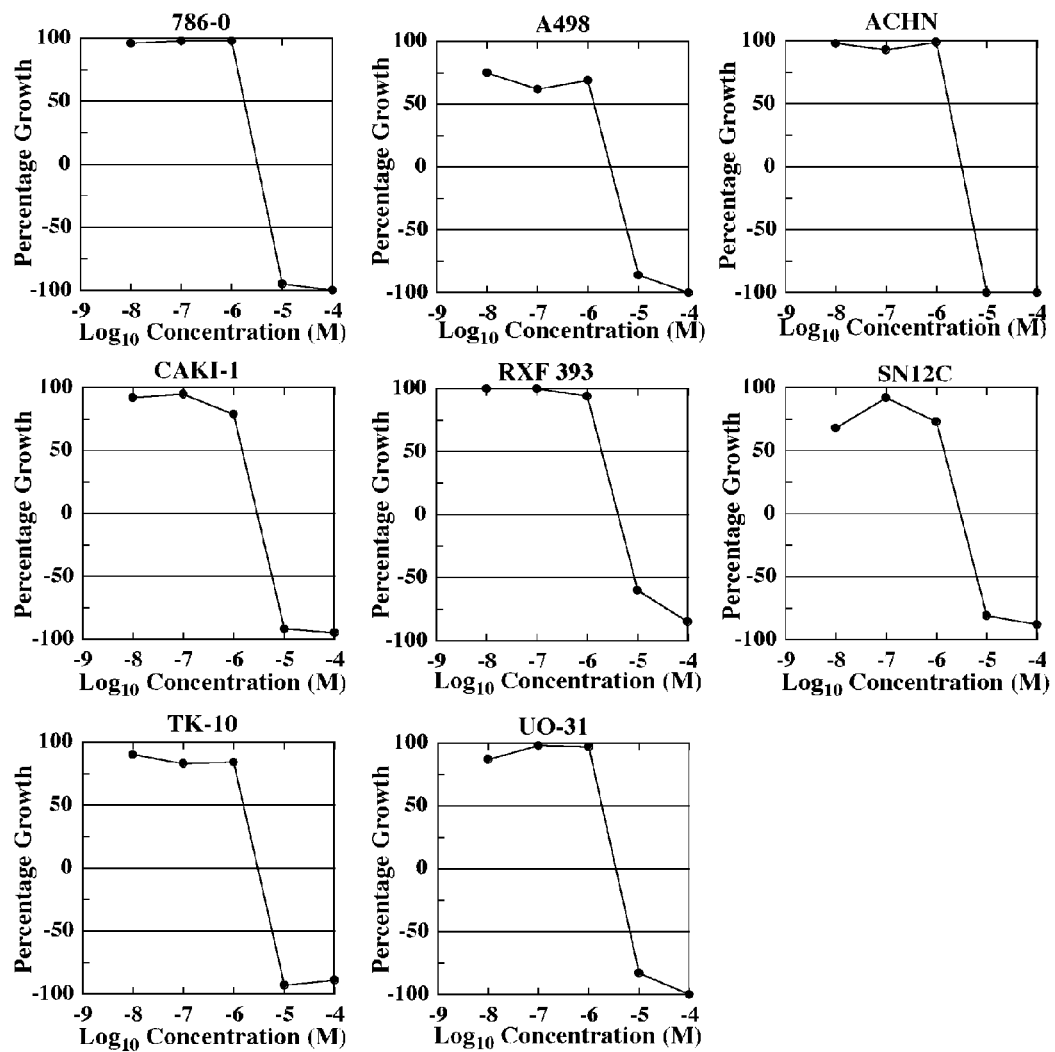
Figure 4H:
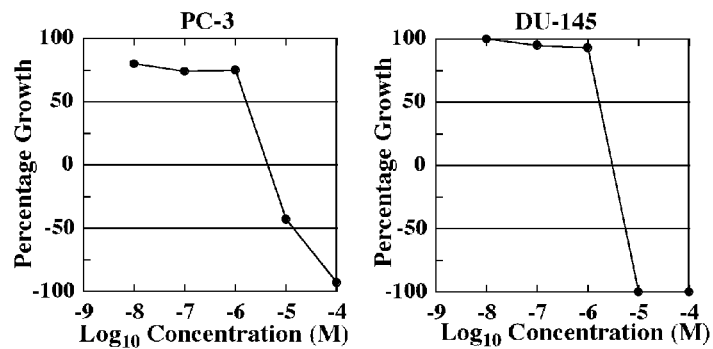
Figure 4I:
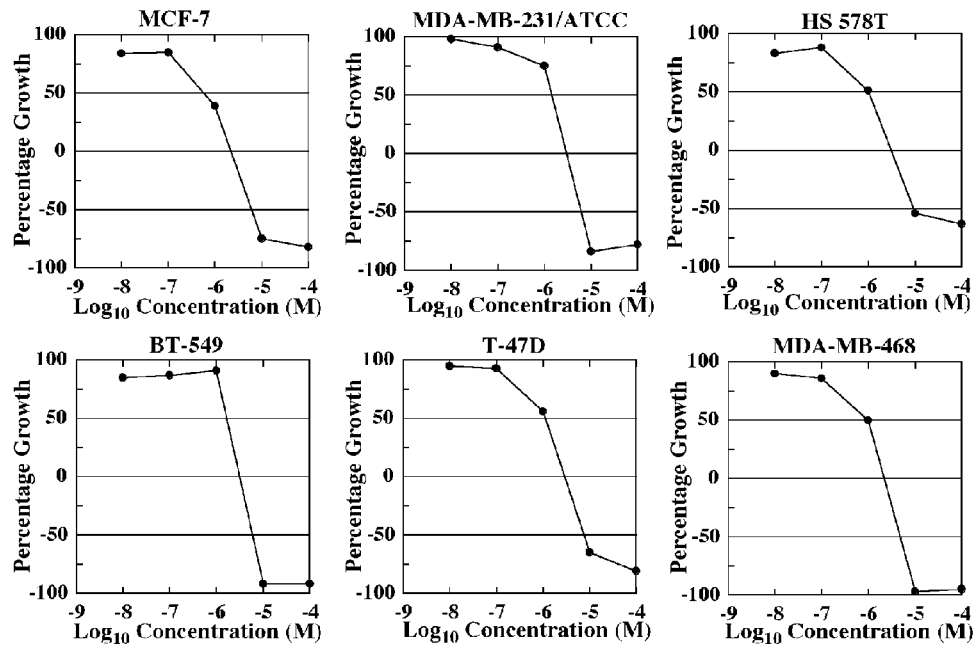

OSU-A9M Administered at 450 ppm in the Diet is Effective in Suppressing PC-3 Xenograft Tumor Growth and is Well Tolerated and without Toxicity Given the increased potency of OSU-A9M compared to the other lead derivatives, an experimental diet was formulated. An AIN-76A rodent diet (American Institute of Nutrition; including primarily casein, sucrose, and corn starch) containing 450 ppm OSU-A9M was made to deliver approximately 50 mg/kg of drug per day to each mouse estimated by food consumption and body weight measurements. Dietary OSU-A9M suppressed the growth of PC-3 xenograft tumors by 59.6% (P<0.05) compared to control mice fed an isocaloric diet lacking the drug (FIG. 3). The body weights of mice receiving the experimental diet were unchanged compared to controls.

Complete cell blood counts and serum chemistry profiles of mice fed the OSU-A9M diet show that none of the measured parameters are affected by drug treatment (Table 2). Further supporting a lack of toxicity with the experimental diet is a preservation of body weight (and liver weight) of mice sacrificed at the conclusion of the 6-week treatment period. 1.3±0.1 g (3.9±0.5%) in drug-treated mice vs. 1.5±0.3 g (4.3±0.7%) in controls; liver percent body weight in parentheses following absolute weight, means±SD, n=7, P=0.1 and 0.5 for absolute and relative values. There was no significant difference in the amount of control or experimental diet consumed by the mice [2.4±0.3 g in drug-treated mice vs. 2.5±0.1 g in controls (P=0.5)]. Throughout the treatment period, the drug-treated mice consumed 34.1±4.6 mg OSU-A9M per kg body weight per day, calculated as g diet consumed per day/g body weight×450 (overall mean±SD of weekly means).

TABLE 2

Hematology and serum chemistry values[a] of nontransgenic male littermates[b] of TRAMP mice fed an AIN-76A rodent diet with or without 450 ppm OSU-A9M from 18 to 24 weeks of age.

|  | Control diet | OSU-A9M 450 ppm |
|---|---|---|
| Hematology | | |
| PCV (%) | 47.0 ± 2.4 | 44.4 ± 1.1 |
| RBC (×$10^6$/μl) | 10.9 ± 0.5 | 10.3 ± 0.3 |
| Nucleated cells (×$10^3$/μl) | 9.8 ± 3.2 | 11.4 ± 3.7 |
| Segmented neutrophils (× $10^3$/μl) | 1.2 ± 0.3 | 1.3 ± 0.5 |
| Lymphocytes (×$10^3$/μl) | 8.2 ± 2.8 | 9.8 ± 3.1 |
| Platelets (×$10^3$/μl) | 101.5 ± 53.8 | 327.2 ± 310.0 |
| Serum Chemistry | | |
| BUN (mg/dl) | 24.0 ± 3.0 | 23.6 ± 2.9 |
| Creatinine (mg/dl) | 0.1 ± 0.0 | 0.1 ± 0.0 |
| Phosphorus (mg/dl) | 7.0 ± 0.6 | 6.5 ± 0.5 |
| Calcium (mg/dl) | 10.8 ± 0.4 | 10.7 ± 0.2 |
| Potassium (mEq/L) | 7.3 ± 0.7 | 6.9 ± 0.4 |
| ALT (iu/L) | 28.8 ± 12.1 | 25.8 ± 8.0 |
| AST (iu/L) | 74.6 ± 25.1 | 69.6 ± 27.2 |
| ALP (iu/L) | 69.0 ± 8.4 | 70.0 ± 14.6 |
| CK (iu/L) | 173.6 ± 153.4 | 222.2 ± 144.5 |
| Cholesterol (mg/dl) | 212.0 ± 33.0 | 193.4 ± 28.1 |
| Total Bilirubin (mg/dl) | 0.2 ± 0.0 | 0.2 ± 0.0 |
| Total Protein (g/dl) | 6.2 ± 0.5 | 5.8 ± 0.3 |
| Albumin (g/dl) | 3.9 ± 0.2 | 3.6 ± 0.2 |
| Globulin (g/dl) | 2.3 ± 0.3 | 2.2 ± 0.1 |
| Glucose (mg/dl) | 251.2 ± 46.4 | 301.8 ± 53.6 |

[a]values represent means ± SD (n = 5)
[b]C57BL/6 × FVB
PCV, packed cell volume;
RBC, red blood cells;
BUN, blood urea nitrogen;
ALT, alanine aminotransferase;
AST, aspartate aminotransferase;
ALP, alkaline phosphatase;
CK, creatine kinase The complete disclosures of the patents, patent documents, and publications cited herein are incorporated by reference in their entirety as if each were individually incorporated, regardless of whether they are individually incorporated by reference. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of formula I:

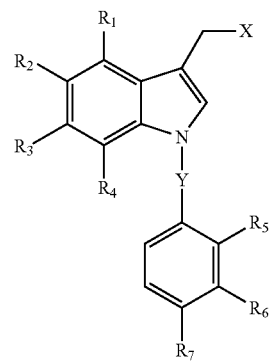

wherein

X is selected from hydroxyl, thiol, and amino;

Y is selected from carboxyl and sulfonyl;

one of $R_1$, $R_2$, $R_3$, and $R_4$ is methyl and the remainder of $R_1$, $R_2$, $R_3$, and $R_4$ are hydrogen; $R_5$ is hydrogen, $R_6$ is nitro, and $R_7$ is chloro; and pharmaceutically acceptable salts thereof.

2. The compound of claim 1, wherein X is hydroxyl.

3. The compound of claim 1, wherein Y is sulfonyl.

4. The compound of claim 1, wherein X is hydroxyl and Y is sulfonyl.

5. The compound of claim 1, wherein $R_2$ is methyl.

6. The compound of claim 1, wherein the compound is selected from

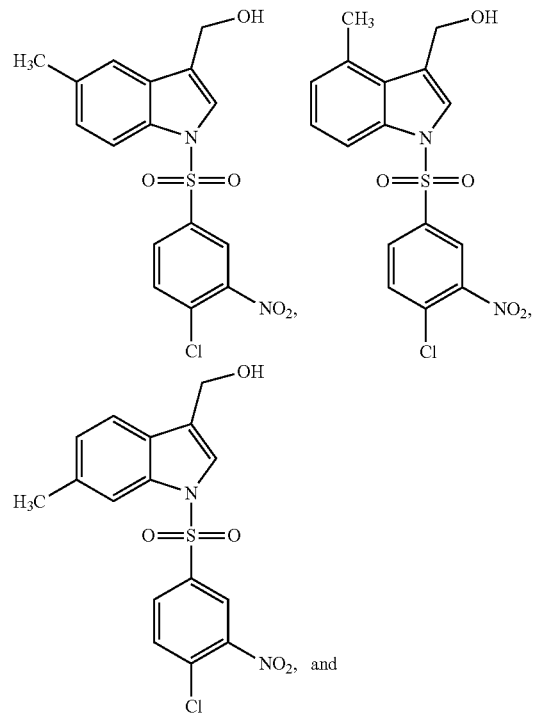

-continued

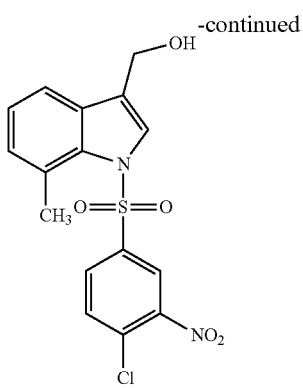

and pharmaceutically acceptable salts thereof.

7. The compound of claim 1, wherein the compound is:

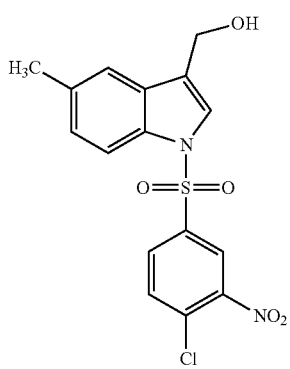

and pharmaceutically acceptable salts thereof.

8. A method of inducing apoptosis in proliferating cells, the method comprising the steps of contacting the proliferating cells with a therapeutically effective amount of a compound of formula I:

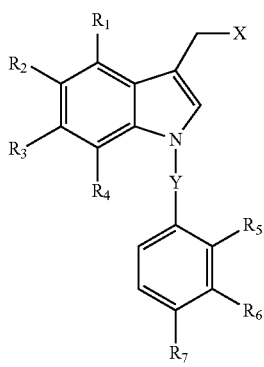

wherein
X is selected from hydroxyl, thiol, and amino;
Y is selected from carboxyl and sulfonyl;
$R_1$, $R_2$, $R_3$, and $R_4$ are selected from hydrogen, lower alkyl, and combinations thereof;
$R_5$, $R_6$, and $R_7$ are selected from hydrogen, halo, nitro, amino, methoxy, and combinations thereof; and pharmaceutically acceptable salts thereof
wherein the proliferating cells are cancer cells and the cancer is selected from prostate cancer, breast cancer, leukemia, non-small cell lung cancer, colon cancer, CNS cancer, melanoma, ovarian cancer, and renal cancer.

9. The method of claim 8, wherein the compound is selected from

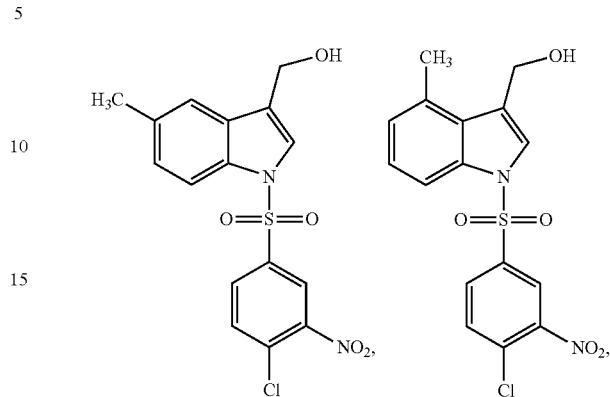

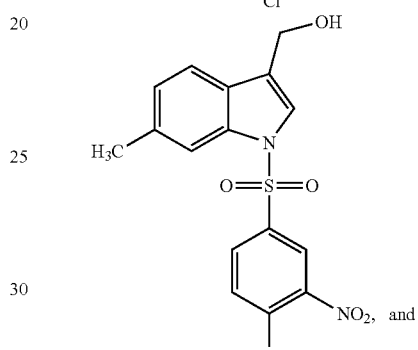

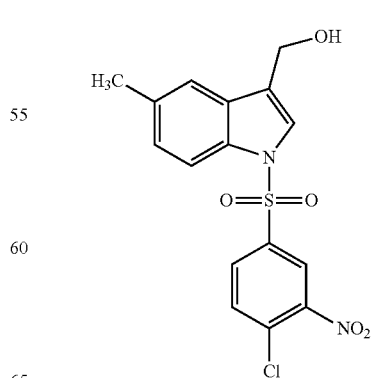

and pharmaceutically acceptable salts thereof.

10. The method of claim 8, wherein the compound is

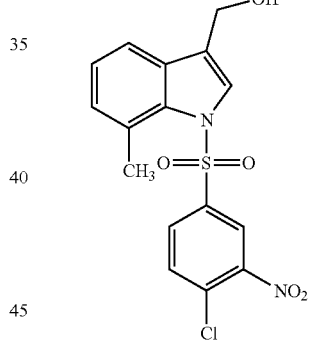

and pharmaceutically acceptable salts thereof.

11. A method of treating cancer in a subject in need thereof, comprising administering to the subject a therapeutically effective amount of a compound of formula I:

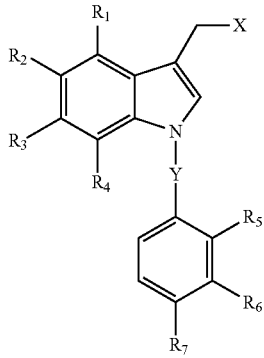

wherein
X is selected from hydroxyl, thiol, and amino;
Y is selected from carboxyl and sulfonyl;
$R_1$, $R_2$, $R_3$, and $R_4$ are selected from hydrogen, lower alkyl, and combinations thereof;
$R_5$, $R_6$, and $R_7$ are selected from hydrogen, halo, nitro, amino, methoxy, and combinations thereof; and pharmaceutically acceptable salts thereof, and
wherein the cancer is selected from the group consisting of prostate cancer, breast cancer, leukemia, non-small cell lung cancer, colon cancer, CNS cancer, melanoma, ovarian cancer, and renal cancer.

12. The method of claim 11, wherein the compound is selected from

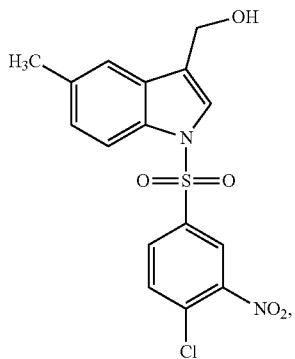 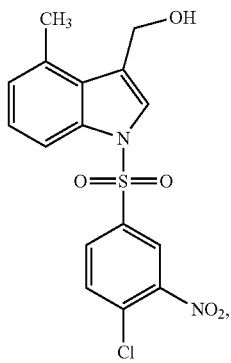

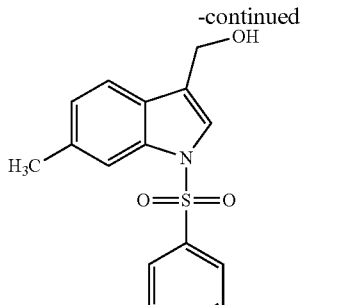

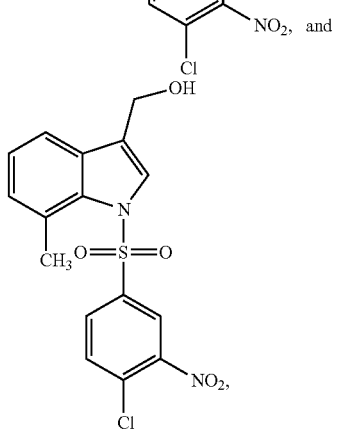

and pharmaceutically acceptable salts thereof.

13. The method of claim 11, wherein the compound is

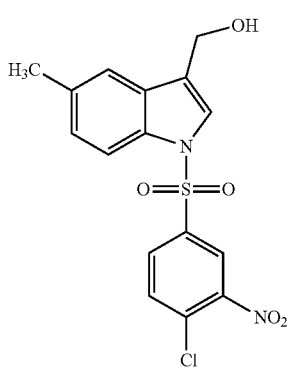

and pharmaceutically acceptable salts thereof.

* * * * *

UNITED STATES PATENT AND TRADEMARK OFFICE
CERTIFICATE OF CORRECTION

| | | |
|---|---|---|
| PATENT NO. | : 8,153,680 B2 | Page 1 of 1 |
| APPLICATION NO. | : 12/547036 | |
| DATED | : April 10, 2012 | |
| INVENTOR(S) | : Chen et al. | |

It is certified that error appears in the above-identified patent and that said Letters Patent is hereby corrected as shown below:

In the Specification

Column 1, Lines 7-10 replace the Government Support Clause with:
--This invention was made with government support under grant numbers CA112250 and CA135560 awarded by the National Institutes of Health. The government has certain rights in the invention.--

Signed and Sealed this
Fifteenth Day of September, 2020

Andrei Iancu
*Director of the United States Patent and Trademark Office*